United States Patent
Phillips et al.

(10) Patent No.: US 9,839,416 B2
(45) Date of Patent: Dec. 12, 2017

(54) HEMOSTATIC DEVICE AND ITS METHODS OF USE

(71) Applicant: Phillips Medical, LLC, Jefferson City, MO (US)

(72) Inventors: Victor Matthew Phillips, Jefferson City, MO (US); Royce Allen Simpson, Kokomo, IN (US)

(73) Assignee: Phillips Medical, LLC, Jefferson City, MO (US)

( * ) Notice: Subject to any disclaimer, the term of this patent is extended or adjusted under 35 U.S.C. 154(b) by 473 days.

(21) Appl. No.: 13/940,766

(22) Filed: Jul. 12, 2013

(65) Prior Publication Data

US 2015/0018871 A1 Jan. 15, 2015

(51) Int. Cl.
*A61B 17/08* (2006.01)
*A61D 1/00* (2006.01)
(Continued)

(52) U.S. Cl.
CPC .. *A61B 17/0057* (2013.01); *A61B 2017/0065* (2013.01); *A61B 2017/00654* (2013.01);
(Continued)

(58) Field of Classification Search
CPC .......... A61B 17/0057; A61B 17/00491; A61B 17/3415; A61B 2017/00371; A61B 2017/00637; A61B 2017/00654; A61B 2017/00004; A61B 2017/00672; A61B 2017/0065; A61B 2017/00659; A61B 2017/00898; A61B 2017/00495;
(Continued)

(56) References Cited

U.S. PATENT DOCUMENTS

| 4,608,965 A | 9/1986 | Anspach, Jr. et al. |
| 4,738,658 A * | 4/1988 | Magro .................. A61M 25/00 604/158 |

(Continued)

FOREIGN PATENT DOCUMENTS

| WO | 0007505 A1 | 2/2000 |
| WO | 03047434 A1 | 6/2003 |

(Continued)

OTHER PUBLICATIONS

An International Search Report and Written Opinion, dated Nov. 12, 2014, for co-pending International application No. PCT/US14/46260 (10 pgs).

(Continued)

*Primary Examiner* — Katherine M Shi
*Assistant Examiner* — Mohamed Gabr
(74) *Attorney, Agent, or Firm* — Armstrong Teasdale LLP

(57) ABSTRACT

A hemostatic device includes a first tube defining a first lumen configured to channel a fluid therethrough, and a second tube housing at least a portion of the first tube and at least partially defining a second lumen configured to retain a hemocoagulant agent therein. The second tube is moveable with respect to the first tube, such that the hemocoagulant agent is at least substantially retained within the second lumen when the second tube is in a first position, and the hemocoagulant agent is at least partially exposed when the second tube is in a second position.

18 Claims, 14 Drawing Sheets

(51) Int. Cl.
*A61B 17/00* (2006.01)
*A61B 90/00* (2016.01)

(52) U.S. Cl.
CPC ........... *A61B 2017/00672* (2013.01); *A61B 2090/0807* (2016.02)

(58) Field of Classification Search
CPC ... A61B 2017/00557; A61B 2090/0811; A61F 2/06; A61F 13/3415; A61F 13/26; A61M 25/0662; A61M 25/04; A61M 2025/0681; A61M 2025/1052; A61M 3/0279
USPC ........................................................ 606/214
See application file for complete search history.

(56) References Cited

U.S. PATENT DOCUMENTS

| | | | |
|---|---|---|---|
| 4,850,960 A | 7/1989 | Grayzel | |
| 4,890,612 A | 1/1990 | Kensey | |
| 4,895,564 A | 1/1990 | Farrell | |
| 4,929,246 A | 5/1990 | Sinofsky | |
| 5,061,274 A | 10/1991 | Kensey | |
| 5,108,421 A | 4/1992 | Fowler | |
| 5,222,974 A | 6/1993 | Kensey et al. | |
| 5,282,827 A | 2/1994 | Kensey et al. | |
| 5,290,310 A * | 3/1994 | Makower | A61B 17/0057 128/DIG. 8 |
| 5,306,254 A | 4/1994 | Nash et al. | |
| 5,324,306 A | 6/1994 | Makower et al. | |
| 5,326,350 A | 7/1994 | Li | |
| RE34,866 E | 2/1995 | Kensey et al. | |
| 5,391,183 A | 2/1995 | Janzen et al. | |
| 5,411,520 A * | 5/1995 | Nash | A61B 17/0057 128/887 |
| 5,415,657 A | 5/1995 | Taymor-Luria | |
| 5,431,639 A * | 7/1995 | Shaw | A61B 17/0057 604/11 |
| 5,437,292 A | 8/1995 | Kipshidze et al. | |
| 5,437,631 A | 8/1995 | Janzen | |
| 5,441,517 A | 8/1995 | Kensey et al. | |
| 5,443,481 A | 8/1995 | Lee | |
| 5,591,204 A | 1/1997 | Janzen et al. | |
| 5,645,566 A | 7/1997 | Brenneman et al. | |
| 5,653,730 A | 8/1997 | Hammerslag | |
| 5,665,107 A | 9/1997 | Hammerslag | |
| 5,676,689 A | 10/1997 | Kensey et al. | |
| 5,707,393 A | 1/1998 | Kensey et al. | |
| 5,716,375 A | 2/1998 | Fowler | |
| 5,725,498 A | 3/1998 | Janzen et al. | |
| 5,741,223 A | 4/1998 | Janzen et al. | |
| 5,766,157 A | 6/1998 | Tilton, Jr. | |
| 5,766,206 A | 6/1998 | Wijkamp et al. | |
| 5,782,861 A | 7/1998 | Cragg et al. | |
| 5,827,304 A | 10/1998 | Hart | |
| 5,843,124 A | 12/1998 | Hammerslag | |
| 5,868,762 A | 2/1999 | Cragg et al. | |
| 5,935,147 A | 8/1999 | Kensey et al. | |
| 5,951,583 A | 9/1999 | Jensen et al. | |
| 5,984,950 A | 11/1999 | Cragg et al. | |
| 6,045,570 A | 4/2000 | Epstein et al. | |
| 6,056,768 A | 5/2000 | Cates et al. | |
| 6,090,130 A * | 7/2000 | Nash | A61B 17/0057 604/168.01 |
| 6,190,360 B1 | 2/2001 | Iancea et al. | |
| 6,254,571 B1 | 7/2001 | Hart | |
| 6,296,657 B1 | 10/2001 | Brucker | |
| 6,302,898 B1 * | 10/2001 | Edwards | A61B 17/00491 606/213 |
| 6,315,753 B1 | 11/2001 | Cragg et al. | |
| 6,325,789 B1 | 12/2001 | Janzen et al. | |
| 6,371,974 B1 | 4/2002 | Brenneman et al. | |
| 6,371,975 B2 | 4/2002 | Cruise et al. | |
| 6,500,152 B1 | 12/2002 | Illi | |
| 6,527,734 B2 | 3/2003 | Cragg et al. | |
| 6,544,236 B1 | 4/2003 | Cragg et al. | |
| 6,547,806 B1 | 4/2003 | Ding | |
| 6,610,026 B2 * | 8/2003 | Cragg | A61B 17/0057 604/15 |
| 6,743,248 B2 * | 6/2004 | Edwards | A61B 17/00491 606/214 |
| 6,818,008 B1 * | 11/2004 | Cates | A61B 17/0057 606/213 |
| 6,830,756 B2 | 12/2004 | Hnojewyj | |
| 6,863,680 B2 | 3/2005 | Ashby | |
| 6,866,669 B2 | 3/2005 | Buzzard et al. | |
| 6,939,352 B2 | 9/2005 | Buzzard et al. | |
| 6,984,219 B2 | 1/2006 | Ashby et al. | |
| 7,029,489 B1 | 4/2006 | Ashby et al. | |
| 7,037,322 B1 * | 5/2006 | Sing | A61B 17/0057 606/213 |
| 7,048,710 B1 | 5/2006 | Cragg et al. | |
| 7,201,725 B1 | 4/2007 | Cragg et al. | |
| 7,318,933 B2 | 1/2008 | Hnojewyj | |
| 7,335,219 B1 | 2/2008 | Ashby et al. | |
| 7,455,680 B1 | 11/2008 | Ashby et al. | |
| 7,476,244 B2 | 1/2009 | Buzzard et al. | |
| 7,611,479 B2 | 11/2009 | Cragg et al. | |
| 7,625,352 B1 | 12/2009 | Ashby et al. | |
| 7,776,062 B2 | 8/2010 | Besselink et al. | |
| 8,088,145 B2 | 1/2012 | Zhu et al. | |
| 8,382,786 B2 | 2/2013 | Besselink et al. | |
| 8,617,253 B2 | 12/2013 | Zhu et al. | |
| 9,179,902 B2 | 11/2015 | Zhu et al. | |
| 9,554,789 B2 | 1/2017 | Overes et al. | |
| 2001/0018598 A1 | 8/2001 | Cruise et al. | |
| 2003/0088271 A1 | 5/2003 | Cragg et al. | |
| 2003/0100921 A1 | 5/2003 | Addis et al. | |
| 2003/0191516 A1 * | 10/2003 | Weldon | A61F 2/95 623/1.12 |
| 2004/0019328 A1 | 1/2004 | Sing et al. | |
| 2004/0098024 A1 | 5/2004 | Dieck et al. | |
| 2004/0102730 A1 | 5/2004 | Davis et al. | |
| 2006/0100664 A1 | 5/2006 | Pai et al. | |
| 2006/0276838 A1 * | 12/2006 | Wensel | A61B 17/0057 606/213 |
| 2007/0038245 A1 | 2/2007 | Morris et al. | |
| 2007/0123816 A1 * | 5/2007 | Zhu | A61B 17/0206 604/57 |
| 2008/0038313 A1 | 2/2008 | Addis et al. | |
| 2008/0046005 A1 * | 2/2008 | Lenker | A61B 17/00491 606/214 |
| 2008/0071310 A1 | 3/2008 | Hoffman et al. | |
| 2008/0082122 A1 | 4/2008 | Khosravi et al. | |
| 2008/0161849 A1 | 7/2008 | Cates et al. | |
| 2009/0088793 A1 | 4/2009 | Bagaoisan et al. | |
| 2009/0143808 A1 | 6/2009 | Houser | |
| 2009/0171282 A1 * | 7/2009 | Pipenhagen | A61B 17/0057 604/103.01 |
| 2009/0312748 A1 * | 12/2009 | Johnson | A61B 17/12022 606/1 |
| 2010/0211000 A1 * | 8/2010 | Killion | A61B 17/00491 604/57 |
| 2011/0137338 A1 * | 6/2011 | Phillips | A61B 17/0057 606/213 |
| 2012/0265243 A1 * | 10/2012 | Phillips | A61B 17/0057 606/213 |
| 2013/0060279 A1 * | 3/2013 | Yassinzadeh | A61B 17/0057 606/213 |
| 2015/0018871 A1 * | 1/2015 | Phillips | A61B 17/0057 606/213 |

FOREIGN PATENT DOCUMENTS

| | | |
|---|---|---|
| WO | 2006093970 A1 | 9/2006 |
| WO | 2008079810 A2 | 7/2008 |
| WO | 2013033477 A1 | 3/2013 |

OTHER PUBLICATIONS

International Search Report and Written Opinion of PCT/US2011/032490; dated Jun. 29, 2011; 10 pages.

(56) References Cited

OTHER PUBLICATIONS

International Search Report and Written Opinion, dated Jan. 12, 2016, for co-pending International Application No. PCT/US2015/040116 (16 pgs.).
An EP Extended Search Report, dated Mar. 1, 2017, for European patent application No. EP 14822893.5 (8 pgs).

* cited by examiner

HEMOSTATIC DEVICE AND ITS METHODS OF USE

BACKGROUND OF THE INVENTION

The subject matter described herein relates generally to medical devices and, more particularly, to a hemostatic device configured to seal a puncture of a vessel.

Catheter introducers are known to provide access to an artery for at least some medical procedures including, without limitation, cardiac catheterizations and peripheral endovascular procedures. After conducting such medical procedures, the catheter introducer is removed from the access site, leaving an arterial opening. At least some body fluids including, without limitation, blood are discharged from the arterial opening. Excess blood loss may endanger and/or traumatize the patient. One known method of controlling blood loss is through direct manual pressure over the arterial opening.

BRIEF SUMMARY OF THE INVENTION

In one aspect, a method is provided for sealing a puncture of a vessel using a hemostatic device that includes a first tube defining a first lumen, and a second tube housing at least a portion of the first tube and at least partially defining a second lumen. The method includes retaining a hemocoagulant agent in the second lumen defined by the second tube. The second tube is in a first position with respect to the first tube. The method further includes advancing the first tube into the vessel until a fluid is channeled through the first lumen defined by the first tube, and selectively moving the second tube towards a second position with respect to the first tube, such that the hemocoagulant is at least partially exposed.

In another aspect, a hemostatic device is provided for sealing a puncture of a vessel. The hemostatic device includes a first tube defining a first lumen configured to channel a fluid therethrough, and a second tube housing at least a portion of the first tube and at least partially defining a second lumen configured to retain a hemocoagulant agent therein. The second tube is moveable with respect to the first tube, such that the hemocoagulant agent is at least substantially retained within the second lumen when the second tube is in a first position, and the hemocoagulant agent is at least partially exposed when the second tube is in a second position.

In yet another aspect, a hemostatic device is provided for sealing a puncture of a vessel. The hemostatic device includes a first tube defining a first lumen configured to channel a fluid therethrough, a second tube housing at least a portion of the first tube and at least partially defining a second lumen configured to retain a hemocoagulant agent therein, and an actuating mechanism configured to move the second tube with respect to the first tube, such that the hemocoagulant agent is at least substantially retained within the second lumen when the second tube is in a first position, and the hemocoagulant agent is at least partially exposed when the second tube is in a second position.

The features, functions, and advantages described herein may be achieved independently in various embodiments of the present disclosure or may be combined in yet other embodiments, further details of which may be seen with reference to the following description and drawings.

DETAILED DESCRIPTION OF THE INVENTION

The methods and apparatus described herein relate to medical devices and, more particularly, to a hemostatic device for use in sealing a puncture of a vessel. The hemostatic device described herein facilitates sealing an opening of a blood vessel. More particularly, in at least one embodiment, the hemostatic device includes a first tube defining a first lumen configured to channel a fluid therethrough, and a second tube housing at least a portion of the first tube and at least partially defining a second lumen configured to retain a hemocoagulant agent therein. The second tube is moveable with respect to the first tube, such that the hemocoagulant agent is at least substantially retained within the second lumen when the second tube is in a first position, and the hemocoagulant agent is at least partially exposed when the second tube is in a second position. The hemocoagulant agent is discharged from the second lumen and seals the opening to reduce a time required for hemostasis and/or ambulation.

As used herein, an element or step recited in the singular and preceded with the word "a" or "an" should be understood as not excluding plural said elements or steps, unless such exclusion is explicitly stated. Further, references to an "embodiment" or an "implementation" are not intended to be interpreted as excluding the existence of additional embodiments or implementations that also incorporate the recited features. Moreover, unless explicitly stated to the contrary, embodiments or implementations "comprising," "including," or "having" an element or a plurality of elements having a particular property may include additional such elements not having that property.

Figure 1:
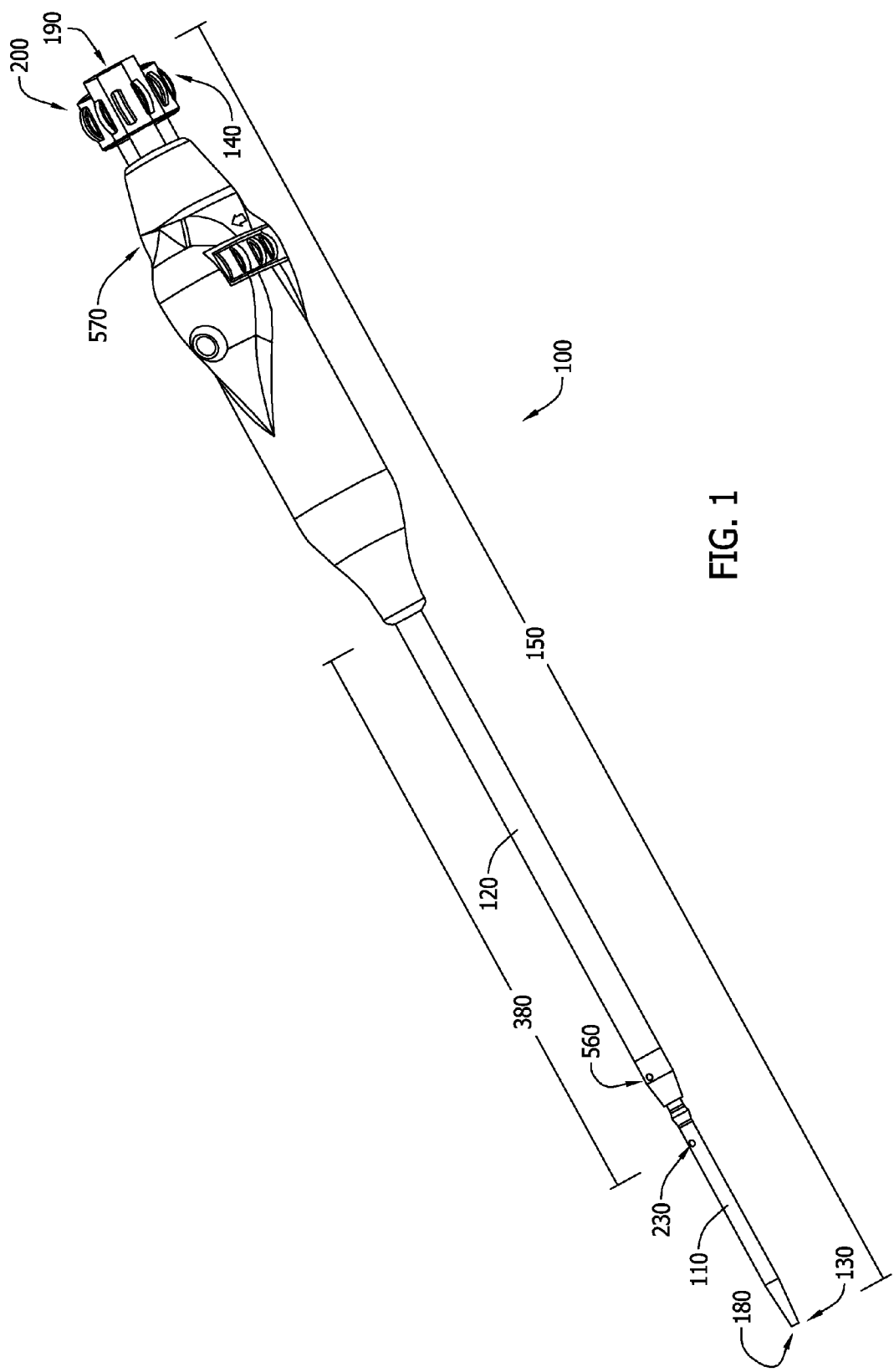
FIG. 1 is a perspective view of an exemplary hemostatic device.

FIG. 1 is a perspective view of an exemplary hemostatic device 100 for sealing a puncture of a vessel (not shown). In the exemplary embodiment, hemostatic device 100 includes a first or inner tube 110 and a second or outer tube 120. In the exemplary embodiment, hemostatic device 100 has a distal end 130, a proximal end 140, and a length 150. In the exemplary embodiment, length 150 is at least approximately 5 inches (in.). More particularly, length 150 is between approximately 8 in. and approximately 12 in. Even more particularly, length 150 is approximately 10.147 in. Alternatively, hemostatic device 100 may have any length that enables the methods and systems to function as described herein. In the exemplary embodiment, a distal end of inner tube 110 is tapered to facilitate traversing through subcutaneous tissue and into a lumen of the vessel.

Figure 2:
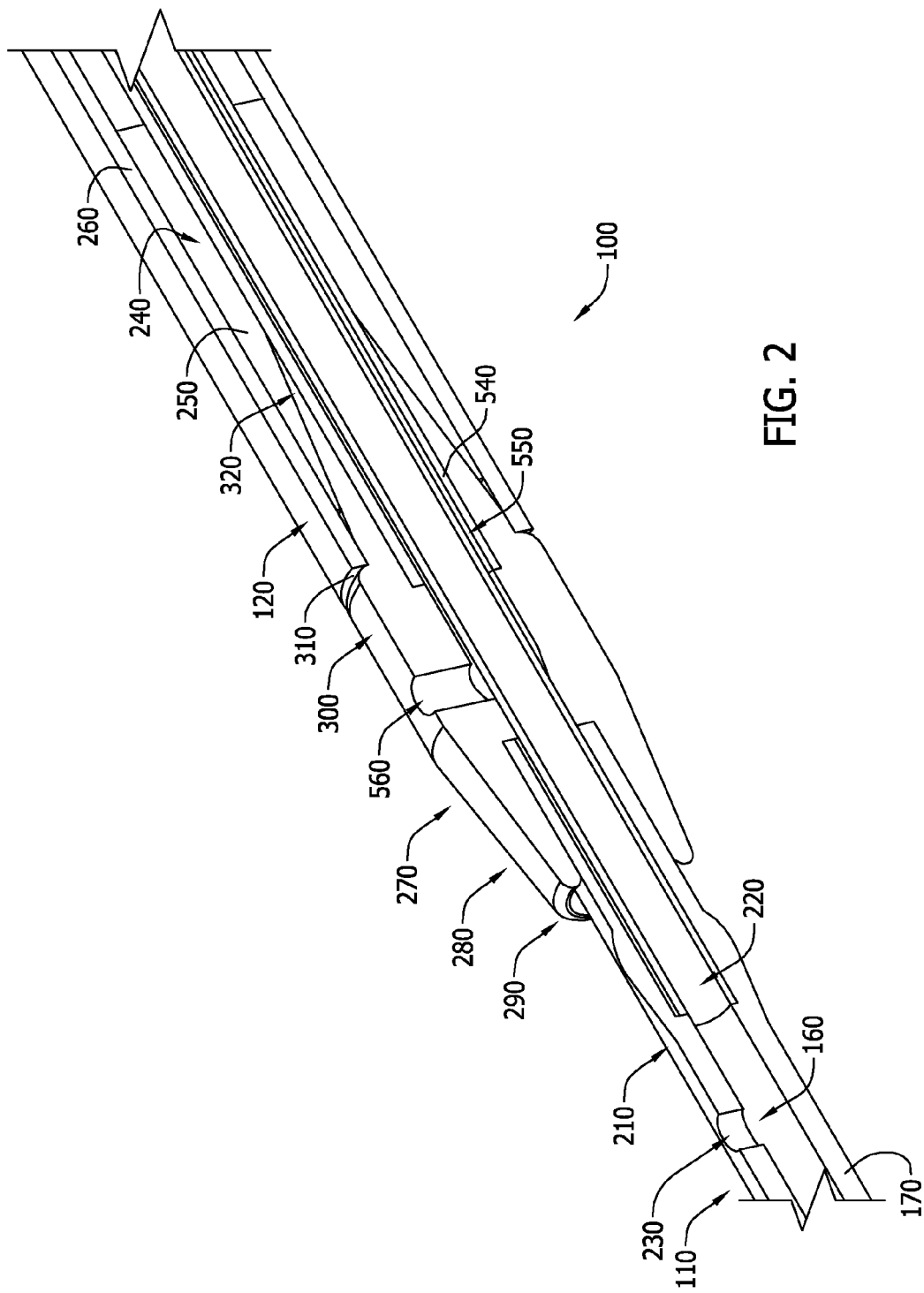
FIG. 2 is a cross-sectional view of a distal portion of the hemostatic device shown in FIG. 1 in a closed configuration.
Figure 3:
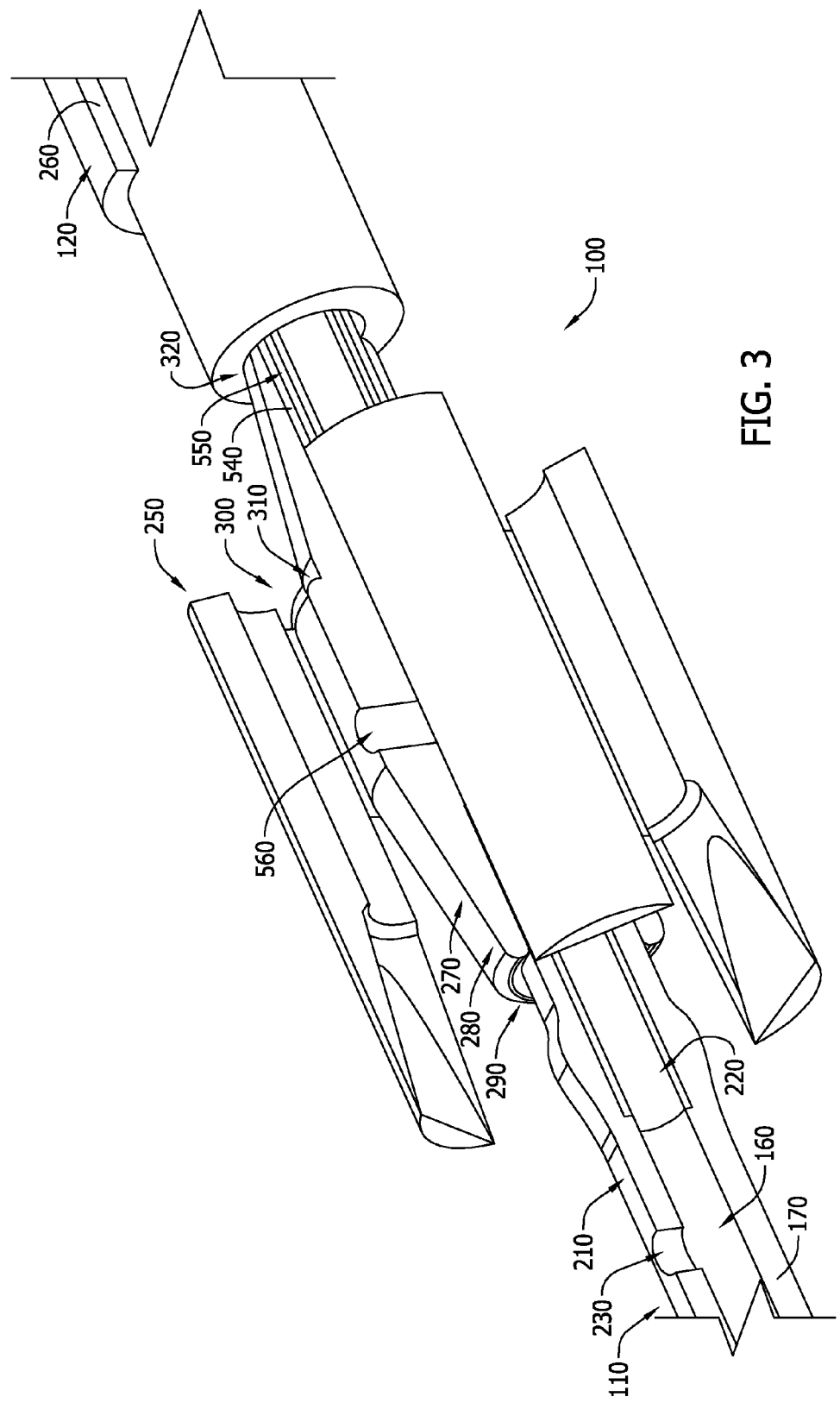
FIG. 3 is a cross-sectional view of the distal portion shown in FIG. 2 in a deployed configuration.

FIG. 2 is a cross-sectional view of a first portion of hemostatic device 100 in a closed configuration, and FIG. 3 is a cross-sectional view of the first portion in a deployed configuration. In the exemplary embodiment, inner tube 110 includes a sidewall 170 that defines a first or inner lumen 160 configured to channel blood or, more broadly, a fluid therethrough. In the exemplary embodiment, sidewall 170 includes a first opening 180 (shown in FIG. 1) at a distal end of inner lumen 160, and a second opening 190 (shown in FIG. 1) at a proximal end of inner lumen 160. In the exemplary embodiment, first opening 180 is sized to receive a guidewire (not shown), and second opening 190 is sized to channel the fluid through inner lumen 160 about the guidewire. First opening 180 and/or second opening 190 may have any size, shape, and/or configuration that enables inner tube 110 to function as described herein.

In the exemplary embodiment, a valve 200 (shown in FIG. 1) proximate to second opening 190 is selectively movable between an open configuration and a closed configuration. More particularly, valve 200 is actuatable towards the closed configuration to selectively restrict access to second opening 190 and/or inner lumen 160. That is, in the exemplary embodiment, valve 200 enables second opening 190 to be at least partially closed such that a flow of the fluid through inner lumen 160 is decreased. Moreover, in the exemplary embodiment, valve 200 is actuatable towards the open configuration to selectively provide access to second opening 190 and/or inner lumen 160. That is, in the exemplary embodiment, valve 200 enables second opening 190 to be at least partially opened such that a flow of the fluid through inner lumen 160 is increased.

In the exemplary embodiment, inner tube 110 includes a distal portion 210 and a proximal portion 220 coupled to distal portion 210 by an interference fit. Alternatively, inner tube 110 may include any number of portions, and/or the portions may be coupled in any configuration and/or using any mechanism that enables inner tube 110 to function as described herein. In the exemplary embodiment, outer tube 120 houses proximal portion 220 of inner tube 110, and distal portion 210 is generally exposed, such that outer tube 120 does not house distal portion 210 of inner tube 110. In the exemplary embodiment, distal portion 210 includes a side opening 230 extending through sidewall 170 that is in fluid communication with inner lumen 160 such that fluid may enter inner lumen 160 through side opening 230.

In the exemplary embodiment, outer tube 120 includes a sidewall 260 that at least partially defines a second or outer lumen 240 (shown in FIG. 2) configured to retain a hemocoagulant agent 250 therein. In one implementation, hemocoagulant agent 250 is an FDA-approved hydrogel polymer or collagen patch. Alternatively, hemocoagulant agent 250 may be any substance and/or composition that enables outer tube 120 to function as described herein.

In the exemplary embodiment, outer tube 120 houses at least a portion of inner tube 110. In the exemplary embodiment, outer tube 120 is translatable or longitudinally moveable with respect to inner tube 110, such that hemocoagulant agent 250 is at least substantially retained within outer lumen 240 when outer tube 120 is in a first or closed position, and is at least partially exposed to the environment when outer tube 120 is in a second or open position. Outer tube 120 is slideable in the distal direction towards the closed position to substantially retain hemocoagulant agent 250 within outer lumen 240, and is slideable in the proximal direction towards the open position to expose hemocoagulant agent 250 to the environment. Alternatively, inner tube 110 and outer tube 120 may move in any direction that enables hemostatic device 100 to function as described herein.

In the exemplary embodiment, hemostatic device 100 includes a plug 270 that at least partially circumscribes inner tube 110. In the exemplary embodiment, plug 270 includes a distal portion 280 having a distal apex 290 oriented towards the distal end of hemostatic device 100, and a proximal portion 300 having a step 310 and a proximal apex 320 oriented towards the proximal end of hemostatic device 100. In the exemplary embodiment, plug 270 is positioned with respect to inner tube 110, such that plug 270 and/or a distal end of outer tube 120 are positionable outside and substantially adjacent an access site and/or a vessel when inner tube side opening 230 is within the lumen of the vessel.

In the exemplary embodiment, plug distal portion 280 is substantially cone-shaped to facilitate traversing plug 270 through subcutaneous tissue, and plug proximal portion 300 is substantially cone-shaped to facilitate channeling or directing hemocoagulant agent 250 radially outward from hemostatic device 100. In the exemplary embodiment, plug proximal portion 300 is oriented and/or configured to channel or direct at least some of hemocoagulant agent 250 away from inner tube 110 and/or a center axis of hemostatic device 100 to facilitate reducing a coagulation of hemocoagulant agent 250 within outer lumen 240.

In the exemplary embodiment, step 310 is configured to interface and/or receive a distal end of outer tube 120, such that hemocoagulant agent 250 is at least substantially retained within outer lumen 240 when hemostatic device 100 is in a closed configuration. Step 310 enables outer tube 120 to be sealingly coupled to plug 270, such that hemocoagulant agent 250 is at least substantially retained within outer lumen 240. In the exemplary embodiment, plug 270 is fabricated at least partially from a soft and/or pliable material that enables a seal to be provided at the plug-outer tube interface, the vessel, and/or the access site. For example, plug 270 may be fabricated from, without limitation, rubber and/or a rubber-like material. Alternatively, plug 270 may have any configuration that enables plug 270 to function as described herein.

Figure 4:
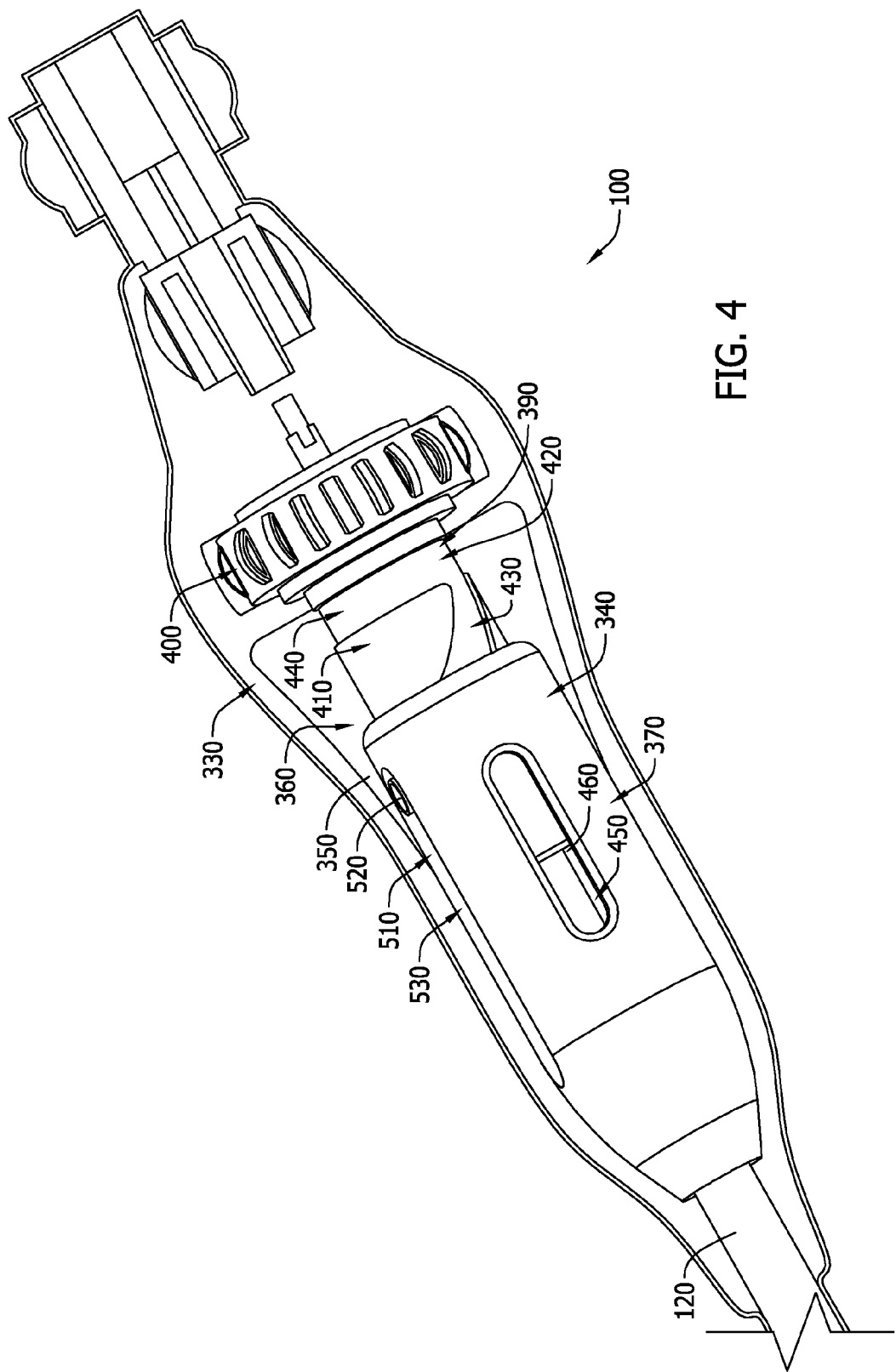
FIG. 4 is a partial cross-sectional view of a proximal portion of the hemostatic device shown in FIG. 1 in a closed configuration.
Figure 5:
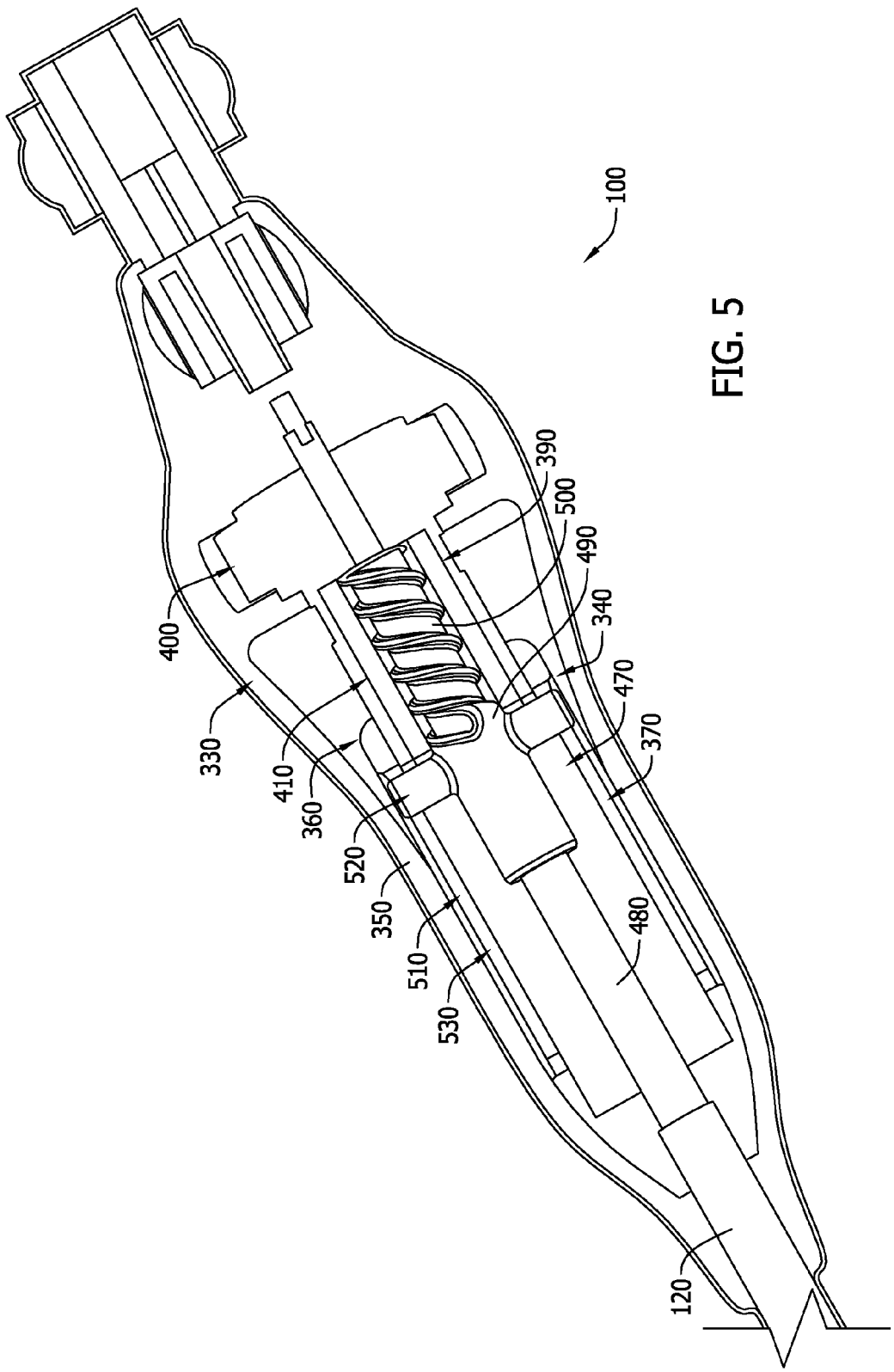
FIG. 5 is a cross-sectional view of the proximal portion shown in FIG. 4.
Figure 6:
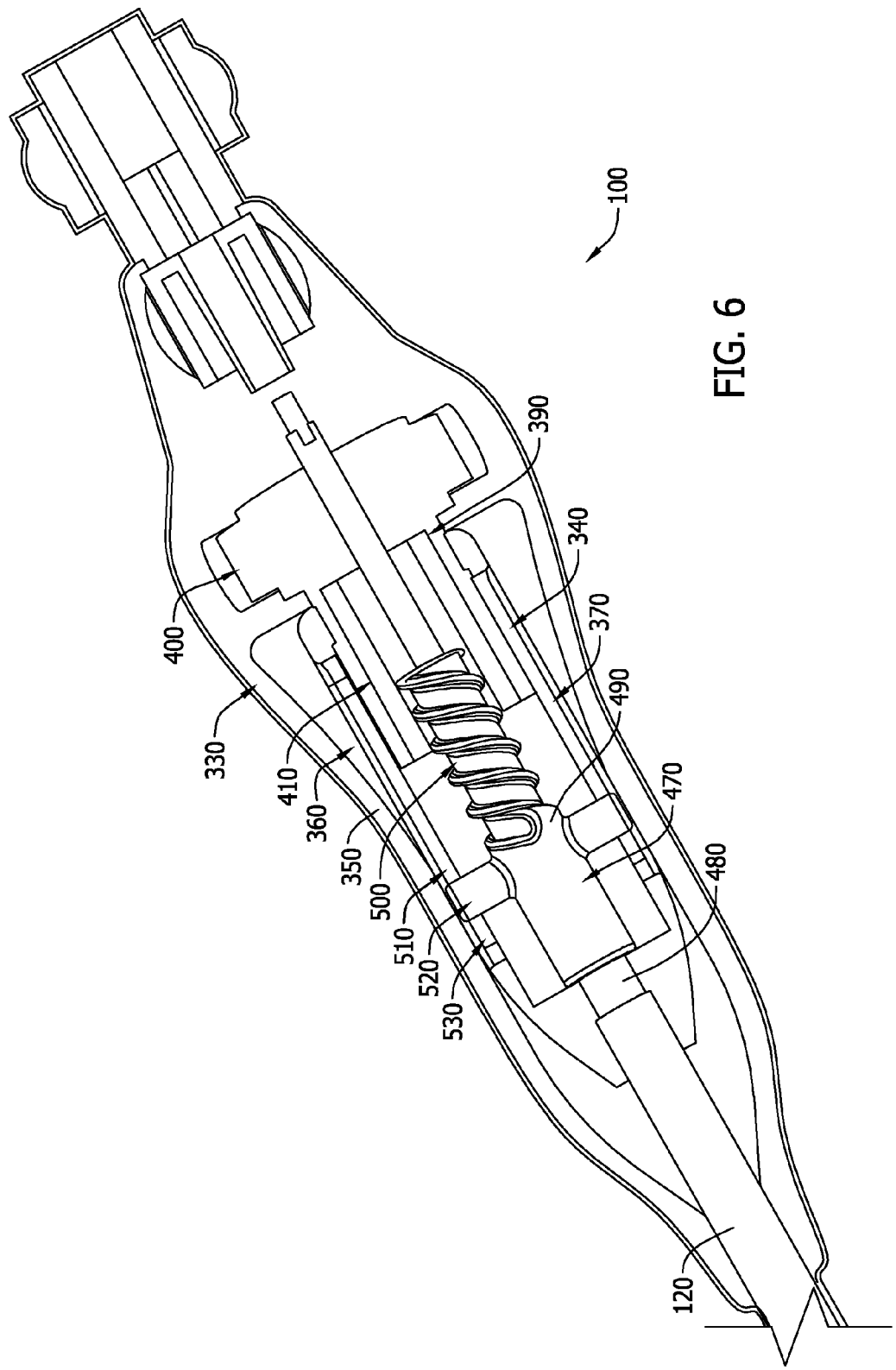
FIG. 6 is a cross-sectional view of the proximal portion shown in FIG. 4 in a deployed configuration.

FIGS. 4 and 5 are cross-sectional views of a second portion of hemostatic device 100 in a closed configuration, and FIG. 6 is a cross-sectional view of the second portion in a deployed configuration. In the exemplary embodiment, hemostatic device 100 includes a housing 330 and an actuating mechanism 340 positioned within housing 330. More specifically, housing 330 includes a sidewall 350 that defines a cavity 360, and actuating mechanism 340 includes a first or an outer tube carrier 370 that is moveable within cavity 360 between a distal end of cavity 360 and a proximal end of cavity 360. In the exemplary embodiment, outer tube carrier 370 is coupled to outer tube 120 such that outer tube 120 moves between the closed position and the open position as outer tube carrier 370 is moved between the distal end of cavity 360 and the proximal end of cavity 360, respectively. Alternatively, outer tube 120 may be moved towards the open position and/or the closed position using any mechanism that enables outer tube 120 to function as described herein.

In the exemplary embodiment, a distance 380 (shown in FIG. 1) between side opening 230 and a distal end of housing 330 is at least approximately 2 in. More particularly, distance 380 is at between approximately 3 in. and approximately 6 in. Even more particularly, distance 380 is approximately 4.2 in. Alternatively, distance 380 may be any length that enables the methods and systems to function as described herein. In the exemplary embodiment, distance 380 remains substantially constant as at least a portion of outer tube 120 is selectively retracted into and/or extended from housing 330 when outer tube 120 is moved between the closed position and the open position.

In the exemplary embodiment, hemostatic device 100 includes a rotating mechanism 390 coupled to outer tube carrier 370. In the exemplary embodiment, rotating mechanism 390 is configured to move outer tube carrier 370 towards the distal end of cavity 360 as rotating mechanism 390 is rotated in a first direction (e.g., a counterclockwise direction when looking from proximal end 140 towards distal end 130) and move outer tube carrier 370 towards the proximal end of cavity 360 as rotating mechanism 390 is rotated in a second direction (e.g., a clockwise direction when looking from proximal end 140 towards distal end 130). Rotating mechanism 390 is configured to convert rotational movement into axial movement. In the exemplary embodiment, rotating mechanism 390 includes a wheel 400 and a body 410 extending from wheel 400 and at least partially positioned within outer tube carrier 370. In the exemplary embodiment, wheel 400 has a diameter that is greater than and/or equal to a width of housing 330.

In the exemplary embodiment, a peg (not shown) extending from an inner surface of outer tube carrier 370 is retained in a groove 420 (shown in FIG. 4) defined in an outer surface of body 410. In the exemplary embodiment, groove 420 includes a first segment 430 (shown in FIG. 4) that extends helically about a central axis of body 410 and a second segment 440 (shown in FIG. 4) that at least partially circumscribes body 410. In the exemplary embodiment, outer tube carrier 370 longitudinally moves with respect to rotating mechanism 390 between the distal end of cavity 360 and the proximal end of cavity 360 as wheel 400 is rotated when the peg is within first segment 430. Moreover, in the exemplary embodiment, outer tube carrier 370 is substantially longitudinally stationary with respect to rotating mechanism 390 as wheel 400 is rotated when the peg is within second segment 440. Alternatively, outer tube carrier 370 may be moved between the distal end of cavity 360 and the proximal end of cavity 360 using any mechanism that enables outer tube 120 to function as described herein. In at least some implementations, second segment 440 fully circumscribes body 410 to enable wheel 400 to be continuously rotated when the peg is within second segment 440. In at least some implementations, outer tube carrier 370 is at the proximal end of cavity 360 when the peg is within second segment 440.

In the exemplary embodiment, hemostatic device 100 includes a first retaining mechanism 450 (shown in FIG. 4) that facilitates preventing outer tube carrier 370 from rotating with respect to housing 330 as wheel 400 is rotated in the first direction and/or in the second direction. In the exemplary embodiment, retaining mechanism 450 includes a peg (not shown) extending from an inner surface of housing 330, and a slot 460 (shown in FIG. 4) defined in an outer surface of outer tube carrier 370 sized to retain the peg. In the exemplary embodiment, slot 460 extends substantially longitudinally along the outer surface of outer tube carrier 370, such that outer tube carrier 370 is longitudinally moveable, while substantially not rotating, with respect to housing 330 as the peg is moved between a distal end of slot 460 and a proximal end of slot 460. Alternatively, outer tube 120 may be moved and/or restricted from movement using any mechanism that enables outer tube 120 to function as described herein.

In the exemplary embodiment, hemostatic device 100 includes a plunging mechanism 470 (shown in FIGS. 5 and 6) including a plunger 480 (shown in FIGS. 2, 3, 5, and 6) at least partially positioned within outer lumen 240 (shown in FIGS. 2 and 3), and a second or plunger carrier 490 (shown in FIGS. 5 and 6) moveable within a cavity defined by outer tube carrier 370 and/or a cavity defined by rotating mechanism body 410 to facilitate discharging hemocoagulant agent 250.

In the exemplary embodiment, a peg (not shown) extending from an inner surface of rotating mechanism body 410 is retained in a groove 500 (shown in FIGS. 5 and 6) defined in an outer surface of plunger carrier 490. In the exemplary embodiment, groove 500 extends helically about a central axis of plunger carrier 490 in a direction that is opposite the direction associated with groove 420. In the exemplary embodiment, plunger 480 is longitudinally moveable, with respect to outer tube 120, in a direction that is opposite the direction outer tube carrier 370 moves with respect to housing 330 as wheel 400 is rotated. For example, in the exemplary embodiment, wheel 400 is selectively rotatable in the first direction to simultaneously move outer tube 120 towards the closed position and plunger 480 towards a retracted or proximal position, or move outer tube 120 towards the open position and plunger 480 towards a dispensing or distal position. Groove 420 extends at a first angle with respect to the longitudinal axis, and groove 500 extends at a second angle that is different from the first angle. The first angle and/or the second angle are predefined, such that outer tube 120 is configured to move a first distance with each rotation of wheel 400, and plunger 480 is configured to move a second distance with each rotation of wheel 400 that is less than the first distance. Alternatively, outer tube 120 and/or plunger 480 may be moved using any mechanism that enables hemostatic device 100 to function as described herein.

In the exemplary embodiment, hemostatic device 100 includes a second retaining mechanism 510 that facilitates preventing plunger carrier 490 from rotating with respect to outer tube carrier 370 as wheel 400 is rotated. In the exemplary embodiment, retaining mechanism 510 includes a peg 520 (shown in FIGS. 5 and 6) extending from an outer surface of plunger carrier 490, and a slot 530 (shown in FIG. 4) defined in an inner surface of outer tube carrier 370 sized to retain peg 520. In the exemplary embodiment, slot 530 extends substantially longitudinally along the inner surface of outer tube carrier 370, such that plunging mechanism 470 is longitudinally moveable, while substantially not rotating, with respect to outer tube carrier 370 as peg 520 is moved between a distal end of slot 530 and a proximal end of slot 530. Alternatively, plunging mechanism 470 may be moved and/or restricted from movement using any mechanism that enables plunging mechanism 470 to function as described herein.

In the exemplary embodiment, hemostatic device 100 includes a third or intermediate tube 540 (shown in FIGS. 2 and 3) positioned radially between inner tube 110 and outer tube 120. More specifically, intermediate tube 540 is positioned such that outer lumen 240 is defined between intermediate tube 540 and outer tube 120, and a third or intermediate lumen 550 (shown in FIGS. 2 and 3) configured to channel blood or, more broadly, a fluid therethrough is defined between intermediate tube 540 and inner tube 110. In the exemplary embodiment, intermediate lumen 550 is in fluid communication with a first opening 560 (shown in FIGS. 1-3) extending through plug 270 and a second opening 570 (shown in FIG. 1) extending through housing 330 such that fluid may enter intermediate lumen 550 through first opening 560 and is dischargeable through second opening 570.

Figure 7:
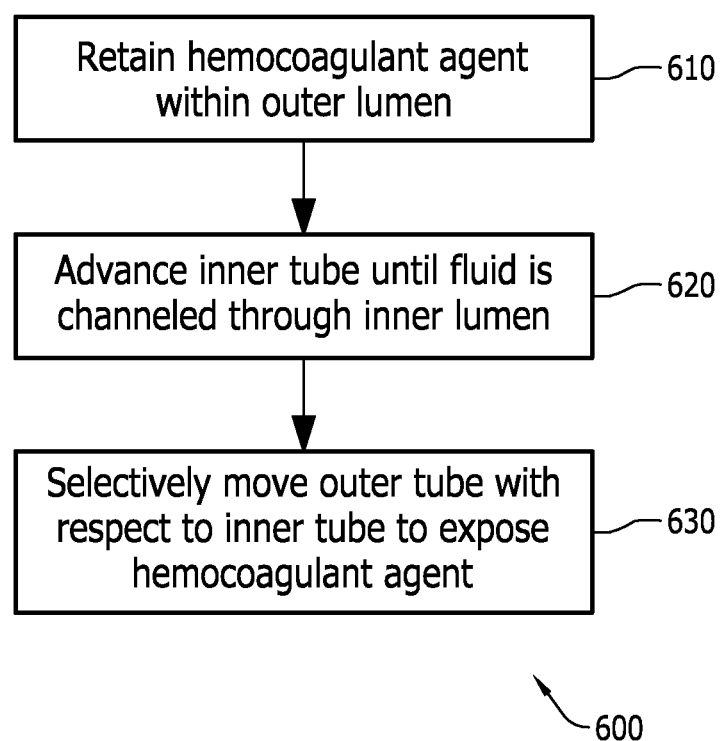
FIG. 7 is a flow chart illustrating an exemplary method of using the hemostatic device shown in FIG. 1.

FIG. 7 is a flow chart illustrating an exemplary method 600 of using hemostatic device 100 to seal a puncture of an artery or vessel with a hydrogel polymer or collagen patch hemocoagulant agent 250. In at least some implementations, hemocoagulant agent 250 is preloaded into hemostatic device 100, such that hemocoagulant agent is retained 610 within outer lumen 240. Alternatively, hemocoagulant agent 250 is loaded into hemostatic device 100, such that hemocoagulant agent is retained 610 within outer lumen 240, by selectively rotating wheel 400 and/or substantially enveloping or circumscribing hemocoagulant agent 250 about inner tube 110.

During operation, inner tube 110 is aligned such that a guidewire (not shown) extends through first opening 180 and second opening 190, and inner tube 110 is advanced 620 along the guidewire through subcutaneous tissue until blood is channeled through inner lumen 160 and/or discharged from second opening 190. In the exemplary embodiment, the blood discharge (i.e., reflux) from second opening 190 is a visual indication that inner tube side opening 230 is positioned within the vessel. Moreover, plug 270 provides a tactile indication (e.g., resistance) that plug 270 is positioned outside and substantially adjacent the vessel and/or inner tube side opening 230 is positioned within the vessel.

In the exemplary embodiment, valve 200 is moved towards the closed configuration to restrict access to second opening 190 and/or facilitate reducing blood flow through inner lumen 160. In at least some implementations, hemostatic device 100 is advanced along the guidewire too far through subcutaneous tissue. In such an implementation, the blood enters plug opening 560, is channeled through intermediate lumen 550, and/or is discharged from housing opening 570. In such an implementation, the blood discharge from housing opening 570 is a visual indication that hemostatic device 100 is advanced too far through subcutaneous tissue and/or should be at least partially withdrawn from the subcutaneous tissue until blood does not discharge from housing opening 570.

In the exemplary embodiment, wheel 400 is selectively rotated in the second direction to move hemostatic device 100 towards the deployed configuration and, thus, move 630 outer tube 120 towards the open position. Accordingly, in the exemplary embodiment, hemocoagulant agent 250 is at least partially exposed to the environment. As wheel 400 is selectively rotated in the second direction, plunger carrier 490 and, thus, plunger 480 is moved in the distal direction, such that hemocoagulant agent 250 is pushed at least partially in the distal direction towards plug 270. In at least some implementations, outer tube 120 is moved 630 towards the open position and plunger 480 is moved towards the distal direction simultaneously. In the exemplary embodiment, plug proximal portion 300 channels or directs at least some of hemocoagulant agent 250 radially outward and/or away from a center axis of hemostatic device 100.

Figure 8:
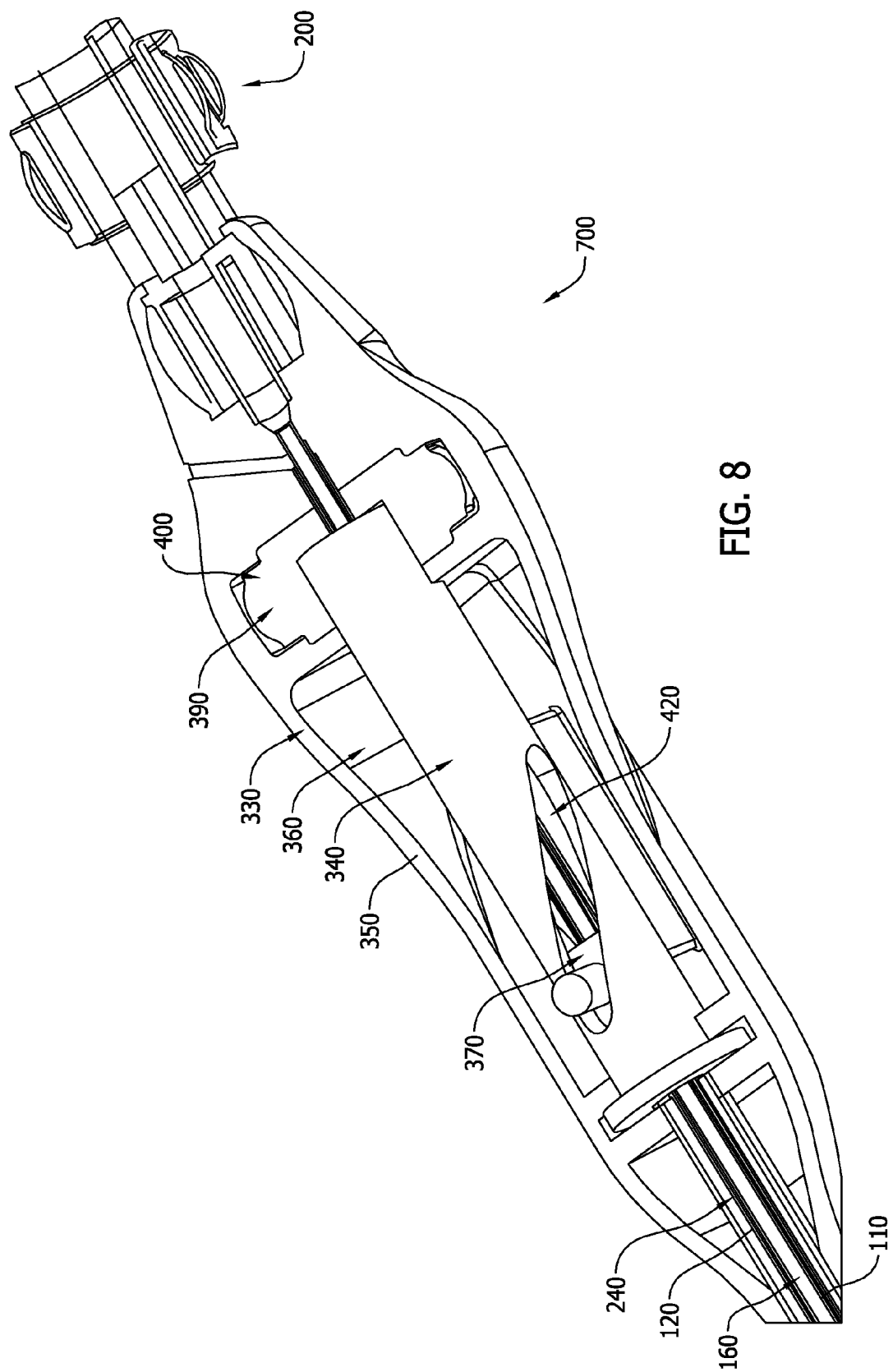
FIG. 8 is a partial cross-sectional view of another exemplary hemostatic device.

FIG. 8 is a partial cross-sectional view of another exemplary hemostatic device 700 for sealing a puncture of a vessel (not shown). Hemostatic device 700 is similar to hemostatic device 100 and, in the absence of a contrary representation, the same reference numbers identify the same or similar elements.

Figure 9:
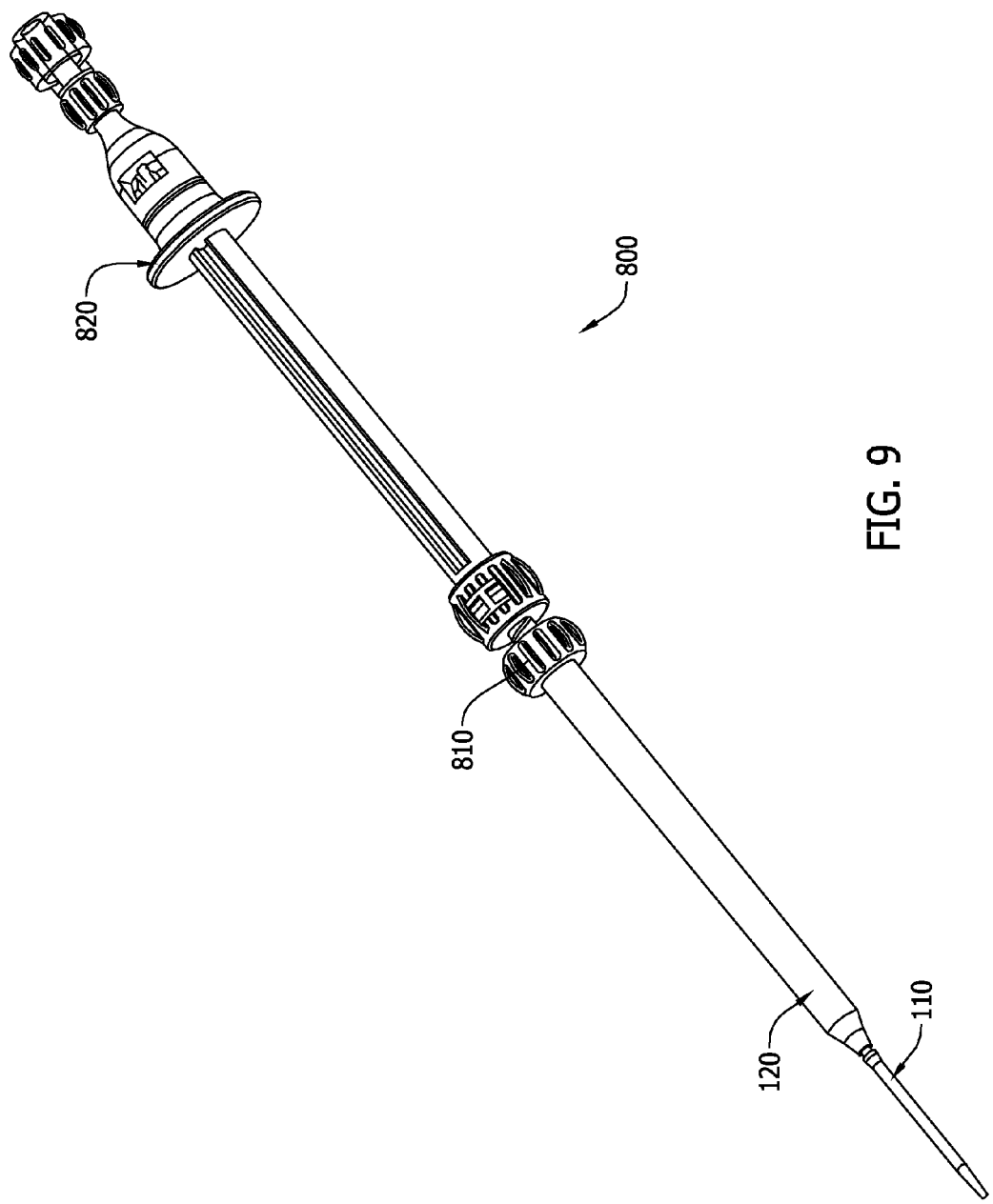
FIG. 9 is a perspective view of yet another exemplary hemostatic device in a closed configuration.
Figure 10:
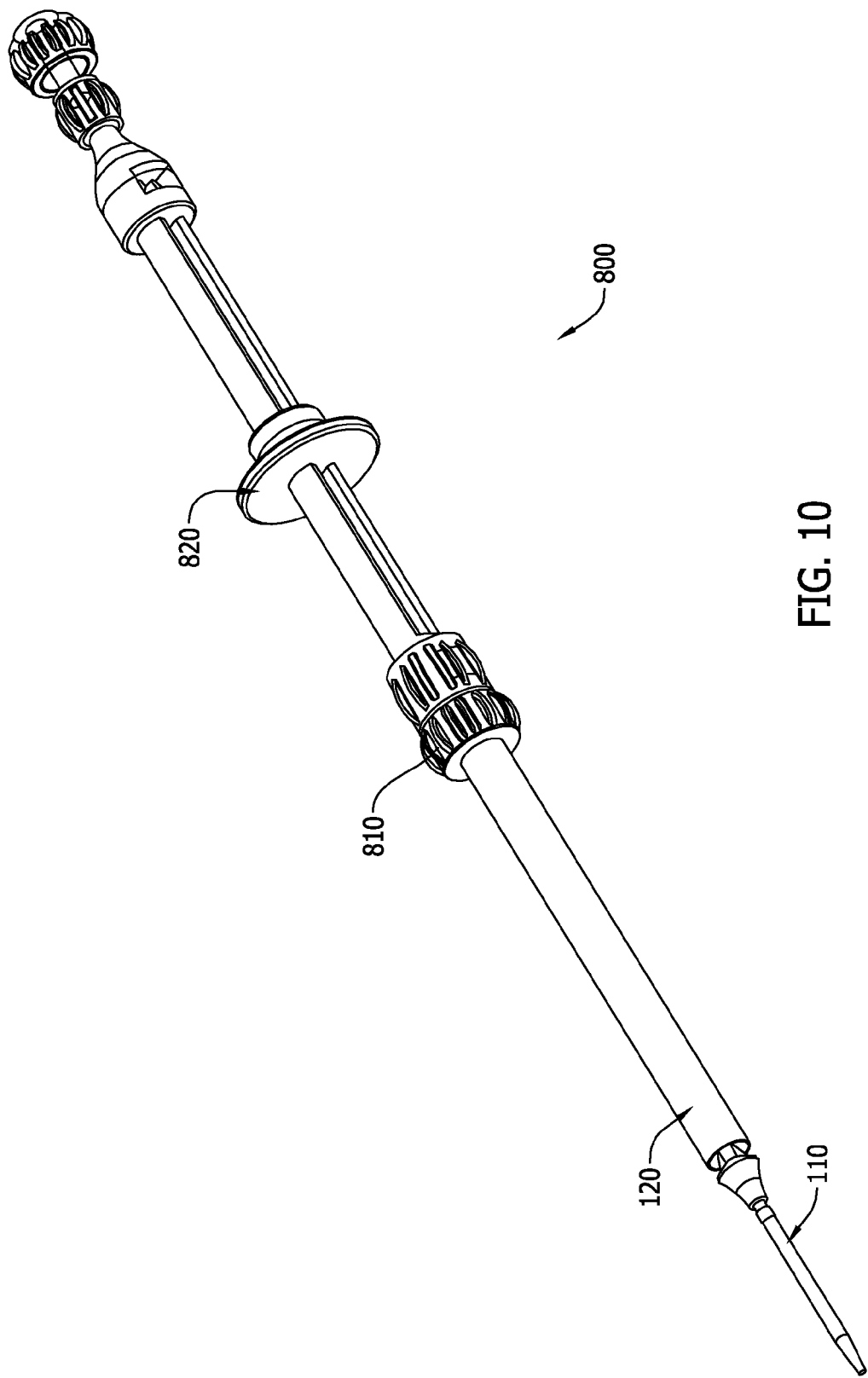
FIG. 10 is a perspective view of the hemostatic device shown in FIG. 9 in an open configuration.

FIG. 9 is a perspective view of another exemplary hemostatic device 800 for sealing a puncture of a vessel (not shown) in a closed configuration, and FIG. 10 is a perspective view of hemostatic device 800 in a deployed configuration. Hemostatic device 800 is similar to hemostatic device 100 and 700 and, in the absence of a contrary representation, the same reference numbers identify the same or similar elements.

In the exemplary embodiment, outer tube 120 is longitudinally moveable with respect to inner tube 110, such that hemocoagulant agent 250 is at least substantially retained within outer lumen 240 when outer tube 120 is in the closed position (shown in FIG. 9), and is at least partially exposed to the environment when outer tube 120 is in the open position (shown in FIG. 10).

Figure 11:
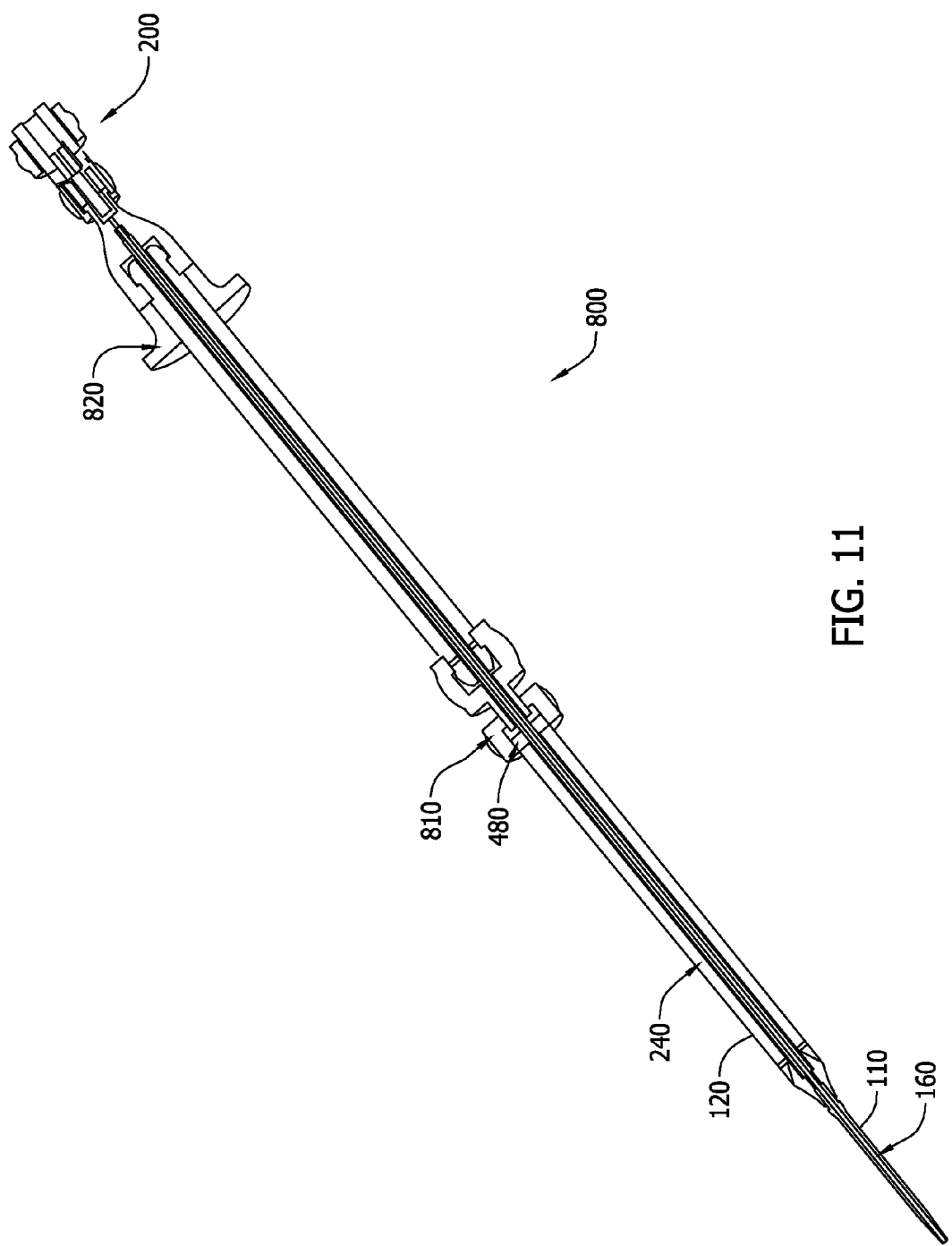
FIG. 11 is a cross-sectional view of the hemostatic device shown in FIG. 9.

FIG. 11 is a cross-sectional view of hemostatic device 800. In the exemplary embodiment, hemostatic device 800 includes an actuating mechanism 810 that facilitates moving outer tube 120 between the closed position and the open position. More specifically, actuating mechanism 810 is rotated in a first direction (e.g., a clockwise direction when looking from proximal end 140 towards distal end 130) to move outer tube 120 towards the closed position, and is rotated in a second direction (e.g., a counterclockwise direction when looking from proximal end 140 towards distal end 130) to move outer tube 120 towards the open position.

In the exemplary embodiment, plunger 480 is moveable within outer lumen 240 to facilitate discharging hemocoagulant agent 250 from outer lumen 240. More specifically, plunger 480 is coupled to a handle 820 (shown in FIGS. 9 and 10) configured to move plunger 480 between a retracted or proximal position and a dispensing or distal position.

Figure 12:
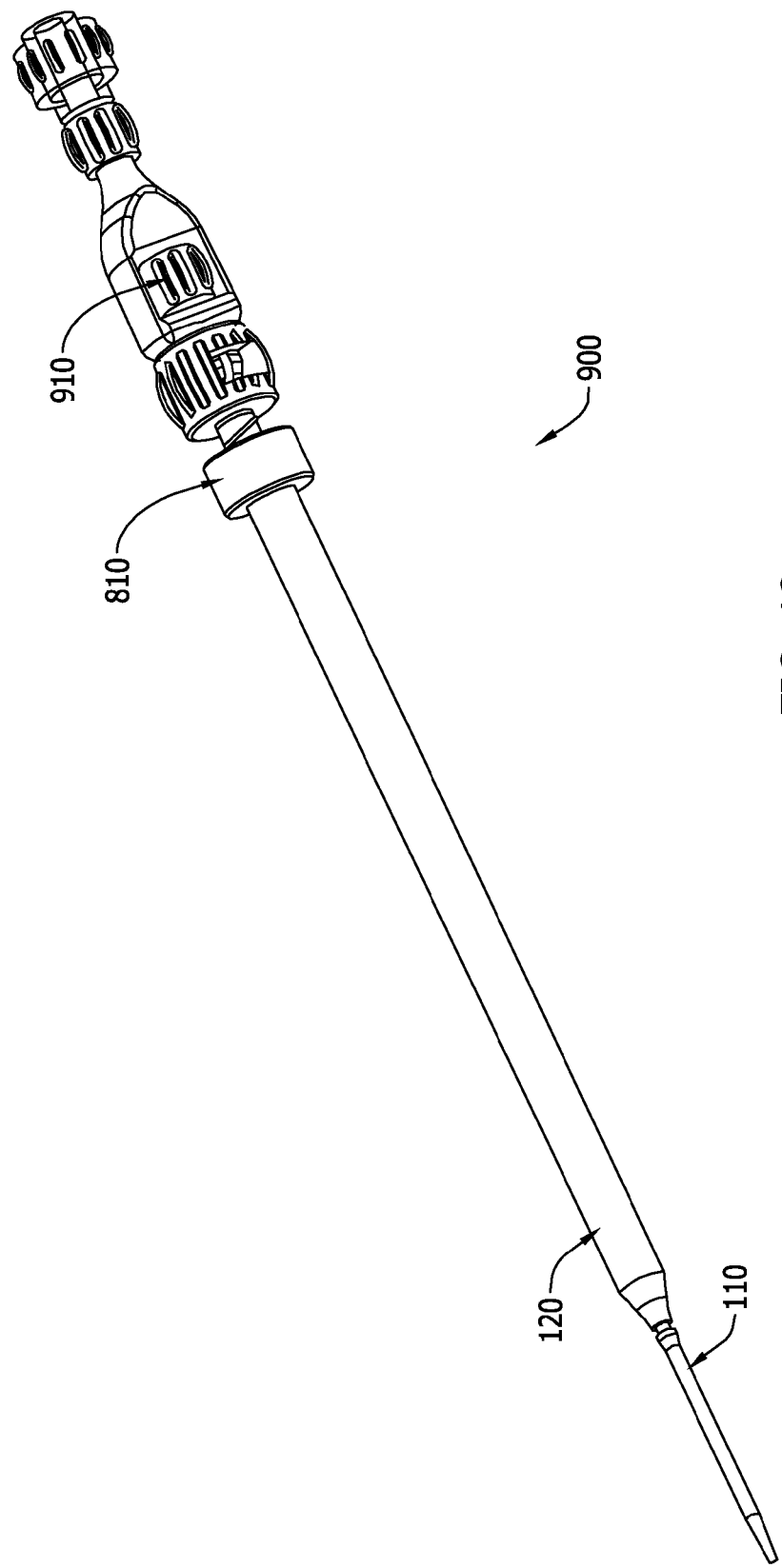
FIG. 12 is a perspective view of yet another exemplary hemostatic device.

FIG. 12 is a perspective view of another exemplary hemostatic device 900 for sealing a puncture of a vessel (not shown). Hemostatic device 900 is similar to hemostatic devices 100, 700, and 800 and, in the absence of a contrary representation, the same reference numbers identify the same or similar elements. In the exemplary embodiment, plunging mechanism 470 includes a wheel 910 configured to move plunger 480 between a retracted or proximal position and a dispensing or distal position.

Figure 13:
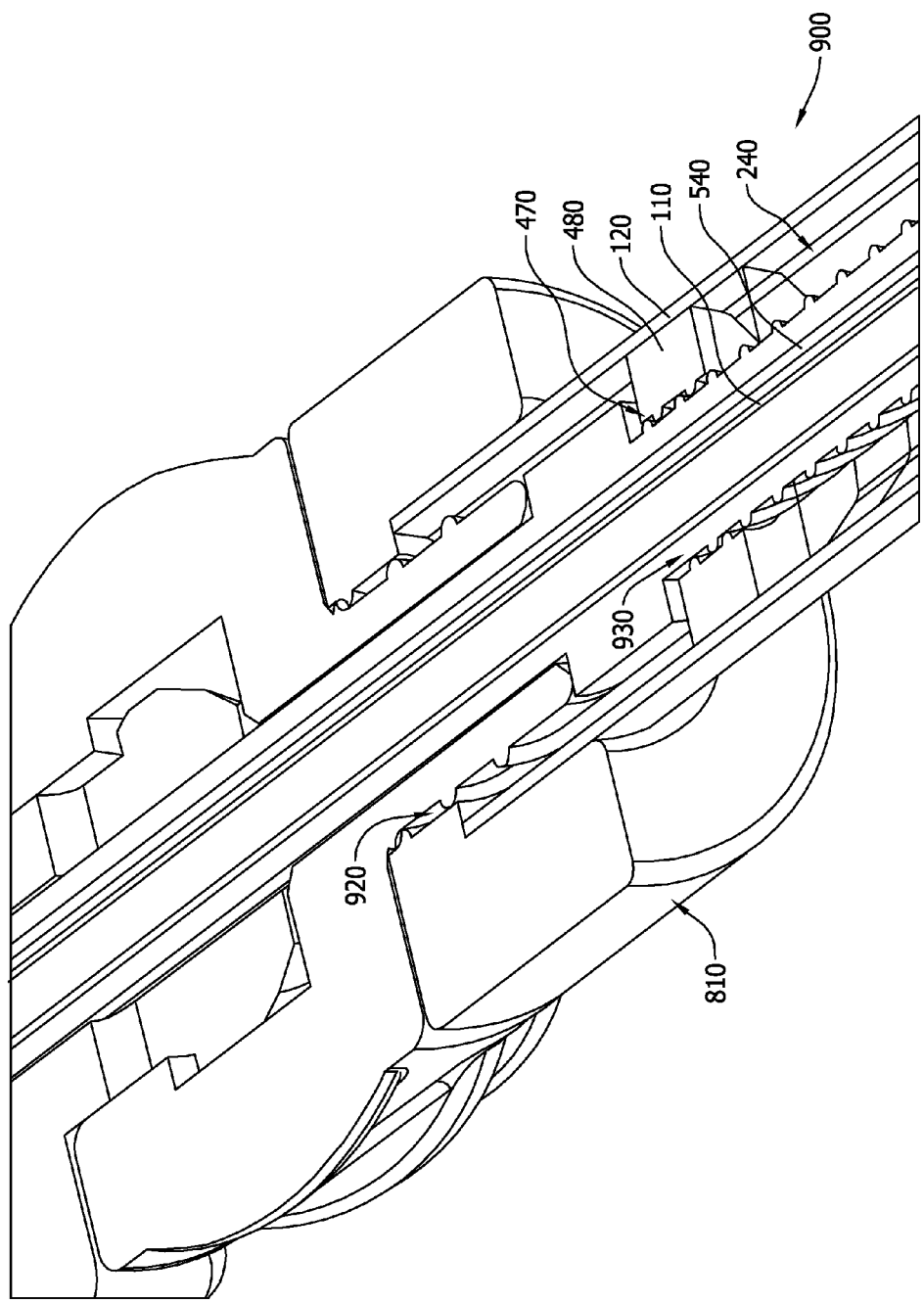
FIGS. 13 and 14 are cross-sectional views of a portion of the hemostatic device shown in FIG. 12.
Figure 14:
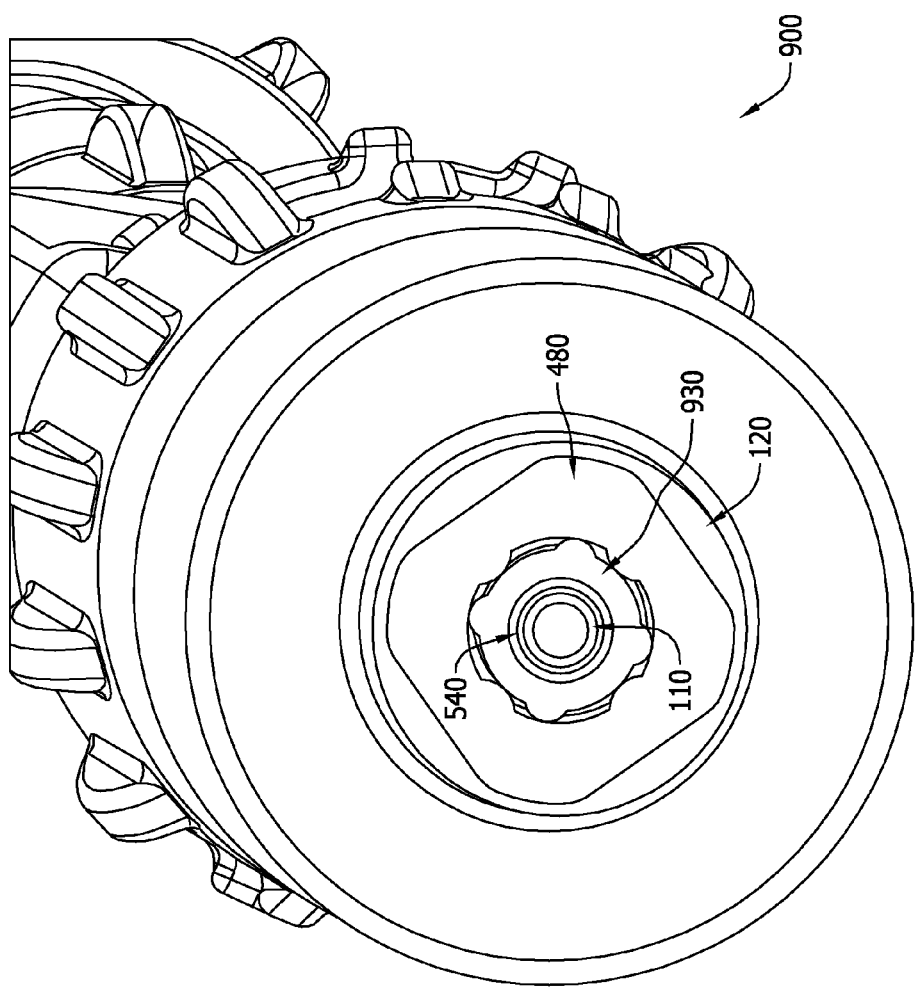

FIGS. 13 and 14 are cross-sectional views of a portion of hemostatic device 800. In the exemplary embodiment, actuating mechanism 810 includes a plurality of threads 920 that enables outer tube 120 to be moved between the closed position and the open position as actuating mechanism 810 is rotated.

In the exemplary embodiment, plunging mechanism 470 includes a plunger shaft 930 coupled to wheel 910, and plunger 480 is threadably coupled to plunger shaft 930. In the exemplary embodiment, an inner surface of outer tube 120 and/or an outer surface of plunger 480 is keyed or otherwise not round (e.g., substantially square-shaped) to prevent plunger 480 from rotating with respect to outer tube 120 as plunger shaft 930 is rotated, such that a rotation of wheel 910 and, thus, plunger shaft 930 longitudinally moves plunger 480 with respect to outer tube 120.

The methods and apparatus described herein relate to medical devices and, more particularly, to a hemostatic device. Hemostatic device described herein facilitates sealing, for example, an arterial opening. The exemplary hemostatic device includes a first tube defining a first lumen configured to channel a fluid therethrough, and a second tube housing at least a portion of the first tube and at least partially defining a second lumen configured to retain a hemocoagulant agent therein. The second tube is at least partially withdrawn to expose at least some of the hemocoagulant agent to the environment while a plunger is moved through the second lumen to facilitate discharging the hemocoagulant agent. The hemocoagulant agent facilitates sealing the arterial opening to reduce a time required for hemostasis and/or ambulation.

Exemplary embodiments of medical devices are described above in detail. The methods and systems are not limited to the specific embodiments described herein, but rather, operations of the methods and components of the systems may be utilized independently and separately from other operations and/or components described herein. For example, the methods and apparatus described herein may have other industrial and/or consumer applications and are not limited to practice with medical devices as described herein. Rather, one or more embodiments may be implemented and utilized in connection with other industries.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A hemostatic device for sealing a puncture of a vessel, said hemostatic device comprising:
    a housing comprising a proximal end and a distal end and defining a cavity therein, said cavity extending between said proximal end and said distal end;
    an outer tube carrier disposed within said cavity, said outer tube carrier moveable within said cavity between said housing distal and proximal ends;
    a first tube defining a first lumen configured to channel a fluid therethrough, said first tube coupled to said housing;
    a second tube extending from said housing distal end, said second tube housing at least a portion of said first tube and at least partially defining a second lumen configured to retain a hemocoagulant agent therein, said second tube coupled to said outer tube carrier and movable therewith relative to said first tube between (i) a closed position configured to substantially retain the hemocoagulant agent within said second lumen when said outer tube carrier is positioned adjacent said housing distal end, and (ii) an open position configured to at least partially expose the hemocoagulant agent when said outer tube carrier is positioned adjacent said housing proximal end;
    a plunger carrier disposed within said cavity, said plunger carrier moveable within said cavity between said housing distal and proximal ends;
    a plunger coupled to said plunger carrier for movement with said plunger carrier, wherein said plunger is longitudinally moveable within said second lumen in response to movement of said plunger carrier within said cavity; and
    an actuating member coupled to, and rotatable with respect to, said housing, said actuating member extending at least partially through said housing, said outer tube carrier and said plunger carrier coupled to said actuating member such that said plunger carrier and said outer tube carrier simultaneously move in opposite directions in response to rotation of said actuating member.

2. A hemostatic device in accordance with claim 1, wherein said outer tube carrier is moveable between said housing proximal and distal ends in response to rotation of said actuating member.

3. A hemostatic device in accordance with claim 1, wherein said actuating member comprises a helical groove, and said outer tube carrier comprises a peg received in said helical groove, said peg and said helical groove cooperative to transform rotational motion of said actuating member into longitudinal translation of said outer tube carrier.

4. A hemostatic device in accordance with claim 3, wherein said plunger carrier comprises a helical groove and said actuating member comprises a peg received in said helical groove, said peg and said helical groove cooperative to transform rotational motion of said actuating member into longitudinal translation of said plunger carrier, said helical groove of said plunger carrier angled oppositely to said helical groove of said actuating member.

5. A hemostatic device in accordance with claim 1, wherein said outer tube carrier comprises a longitudinally extending slot, and said housing comprises a retaining peg received in said longitudinally extending slot, said retaining peg and said longitudinally extending slot cooperative to prevent said outer tube carrier from rotating with respect to said housing.

6. A hemostatic device in accordance with claim 1, wherein said plunger is longitudinally moveable within said second lumen in response to movement of said plunger carrier from adjacent said housing proximal end to adjacent said housing distal to facilitate discharging the hemocoagulant agent.

7. A hemostatic device in accordance with claim 1, wherein said outer tube carrier comprises a longitudinally extending slot, and said plunger carrier comprises a retaining peg received in said longitudinally extending slot, said retaining peg and said longitudinally extending slot cooperative to prevent said plunger carrier from rotating with respect to said outer tube carrier.

8. A hemostatic device in accordance with claim 1, wherein said first tube further comprises a first side opening in fluid communication with said first lumen, wherein a distance between said first side opening and said housing remains constant as said outer tube carrier is moved between said distal and proximal ends of said cavity.

9. A hemostatic device in accordance with claim 1 further comprising a plug positioned proximate a distal end of said second lumen, said first tube coupled to said plug and extending therethrough, said plug configured to channel the hemocoagulant agent radially outward from said first tube.

10. A hemostatic device for sealing a puncture of a vessel, said hemostatic device comprising:
    a housing comprising a proximal end and a distal end and defining a cavity therein, said cavity extending between said proximal end and said distal end;
    a first tube defining a first lumen configured to channel a fluid therethrough, said first tube coupled to said housing;
    a second tube extending from said housing distal end, said second tube movable longitudinally relative to said first tube, said second tube housing at least a portion of said first tube and at least partially defining a second lumen configured to retain a hemocoagulant agent therein;

a plunger extending from said housing distal end, said plunger longitudinally moveable within said second lumen; and an actuating member coupled to said housing, said plunger, and said second tube such that said plunger and said second tube simultaneously move in longitudinally opposite directions in response to rotation of said actuating member, said actuating member configured to move said second tube with respect to said first tube between (i) a closed position configured to substantially retain the hemocoagulant agent within said second lumen, and (ii) an open position configured to at least partially expose the hemocoagulant agent.

11. A hemostatic device in accordance with claim 10, wherein said actuating member is rotatable in a first direction to move said second tube distally, and in a second direction to move said second tube proximally.

12. A hemostatic device in accordance with claim 10 further comprising a plunger carrier disposed within said cavity, said plunger carrier moveable within said cavity between said housing distal and proximal ends, said plunger coupled to said plunger carrier for movement with said plunger carrier, wherein said plunger is longitudinally moveable within said second lumen in response to movement of said plunger carrier between said housing distal and proximal ends.

13. A hemostatic device in accordance with claim 12 further comprising an outer tube carrier disposed within said cavity, said outer tube carrier moveable within said cavity between said housing distal and proximal ends, said second tube coupled to said outer tube carrier for movement with said outer tube carrier, wherein said second tube is longitudinally moveable relative to said first tube in response to movement of said outer tube carrier between said housing distal and proximal ends.

14. A hemostatic device for sealing a puncture of a vessel, said hemostatic device comprising:
   a housing comprising a proximal end and a distal end and defining a cavity therein, said cavity extending between said proximal end and said distal end;
   an outer tube carrier disposed within said cavity, said outer tube carrier moveable within said cavity between said distal end and said proximal end;
   a first tube defining a first lumen configured to channel a fluid therethrough, said first tube coupled to said housing;
   a second tube extending from said housing distal end, said second tube housing at least a portion of said first tube and at least partially defining a second lumen configured to retain a hemocoagulant agent therein, said second tube coupled to said outer tube carrier and movable therewith relative to said first tube between (i) a closed position configured to substantially retain the hemocoagulant agent within said second lumen when said outer tube carrier is positioned adjacent said housing distal end, and (ii) an open position configured to at least partially expose the hemocoagulant agent when said outer tube carrier is positioned adjacent said housing proximal end;
   a plunger carrier disposed within said cavity, said plunger carrier moveable between said housing distal and proximal ends; and
   a plunger coupled to said plunger carrier for movement with said plunger carrier, wherein said plunger is longitudinally moveable within said second lumen in response to movement of said plunger carrier between said housing distal and proximal ends to facilitate discharging the hemocoagulant agent, wherein said outer tube carrier comprises a longitudinally extending slot, and said housing comprises a retaining peg received in said longitudinally extending slot, said retaining peg and said longitudinally extending slot cooperative to prevent said outer tube carrier from rotating with respect to said housing.

15. A hemostatic device in accordance with claim 14, wherein said plunger carrier and said outer tube carrier are coupled to an actuating member such that said plunger carrier and said outer tube carrier simultaneously move in opposite directions in response to rotation of said actuating member.

16. A hemostatic device in accordance with claim 15, wherein said actuating member comprises a helical groove, and said outer tube carrier comprises a peg received in said helical groove, said peg and said helical groove cooperative to transform rotational motion of said actuating member into longitudinal translation of said outer tube carrier.

17. A hemostatic device in accordance with claim 14, wherein said first tube further comprises a first side opening in fluid communication with said first lumen, wherein a distance between said first side opening and said housing remains constant as said outer tube carrier is moved between said distal and proximal ends of said cavity.

18. A hemostatic device in accordance with claim 14 further comprising a plug positioned proximate a distal end of said second lumen, said first tube coupled to said plug and extending therethrough, said plug configured to channel the hemocoagulant agent radially outward from said first tube.

* * * * *